United States Patent
Sun et al.

(10) Patent No.: US 6,277,968 B1
(45) Date of Patent: *Aug. 21, 2001

(54) HUMAN UROPLAKIN II GENE AND METHODS FOR DETECTING AND CLASSIFYING BLADDER CANCER VIA HUMAN UROPLAKIN GENES

(75) Inventors: Tung-Tien Sun, Scarsdale; Xue-Ru Wu, New York, both of NY (US)

(73) Assignee: New York University, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/969,317

(22) Filed: Nov. 13, 1997

(51) Int. Cl.[7] .......................... C07H 21/02; C07H 21/04; C12Q 1/68; C12P 19/34
(52) U.S. Cl. ..................... 536/23.1; 536/23.5; 435/6; 435/7.1; 435/91.1; 435/91.2
(58) Field of Search ................................ 435/6, 7.1, 91.1, 435/91.2; 536/23.1, 23.5

(56) References Cited

PUBLICATIONS

Wu et al, Uroplakin II is expressed in transitional cell carc., Cancer Research 58(6) 1291–7, 1998.*
Ogawa et al, Analysis of different. assoc. proteins in rat bladder Carcinogenesis 17 (5) 961–5, 1996.*
Meyer–Puttlitz et al, Ectopic expression of bact lacZ gene in limbic sys. NeuroReport 6 (12) 1674–8, 1995.*
Cordon–Cardom C. et al. "P53 Mutations In Human Bladder Cancer: Genotypic Versus Phenotypic Patterns", 1994. Int. J. Cancer 56:347–353.
Landis, R.J. et al., "Average Partial Association in Three–way Contingency Tables: a Review and Discussion of Alternative Tests", 1978 Int. Stat. Rev. 46:237–254.
Lin, J.H. et al. "Precursor Sequence, Processing, and Urothelium–specific Expression of a Major 15–kDa Protein Subunit of Asymmetric Unit Membrane", 1994, J. Biol. Chem. 269:1775–1784.
Metha, C.R. and Patel, N.R., "A Networth Algorithm for Performing Fisher's Exact Test in r x c Contingency Tables", 1983, J. Am. Stat. Assoc. 78:427–434.
Moll, et al., "Uroplakin III, ein spezifisches Membranprotein von urothelialen Deckzellen, als histologischer Market fur metastatische Urothelkarzinome", 1993. Verh. Deutsc. Ges. Path. 77.
Moll, R. et al., "Uroplakins, Specific Membrane Proteins of Urothelial Umbrella Cells, as Histological Markers of Metastatic Transitional Cell Carcinomas", 1995. Am. J. Pathol. 147:1383–1397.

Orita, M. et al., Rapid and Sensitive Detection of Point Mutations and DNA Polymorphisms Using the Polymerase Chain Reaction, 1989. Genomics 5:874–879.
Osman, I. et al., Alterations Affecting the p53 Control Pathway in Bilharzial–related Bladder Cancer [1] 1997. Clin. Can. Res. 3:531–536.
Ryan et al., "Chromosomal localization of uroplakin genes of cattle and mice", 1993. Mammalian Genome 4:656–661.
Sanger, F. et al., "DNA sequencing with chain–terminating inhibitors", 1977. Proc. Natl Acad. Sci. USA 74:5463–5467.*
Stokke, T. et al., A Physical Map of Chromosome 20 Established Using Fluorescence in Situ Hybridization and Digital Image Analysis, 1995 Genomics 26:134–7.*
Summerhayes et al., Monoclonal Antibodies Raised Against Cell Membrane Components of Human Bladder Tumor Tissue Recognizing Subpopulations in Normal Urothelium, 1985. JNCI 75:1025–1038.*
Wu et al., "Large Scale Purification and Immunolocalization of Bovine Uroplakins I, II, and III", 1990, J. Biol. Chem. 265:19170–19179.*
Wu et al., "Molecular cloning of a 47 kDa tissue–specific and differentiation–dependent urothelial cell surface glycoprotein", 1993. J. Cell. Sci. 106:31–43.*
Wu et al., "Mammalian Uroplakins", 1994, J. Biol. Chem. 269:13716–13724.*
Wu, X.R. et al., "Selective Interactions of UPIa and UPIb, Two Members of the Transmembrane 4 Superfamily, with Distinct Single Transmembrane–domained Proteins in Differentiated Urothelial Cells" 1995. J. Biol. Chem. 270:29752–29759.*
Yu et al., "Uroplakin I: A 27–kD Protein Associated with the Asymmetric Unit Membrane of Mammalian Urothelium", 1990, J. Cell Biol. 111:1207–1216.*
Yu et al., "Identification of an 85–100 kDa Glycoprotein as a Cell Surface Marker for an Advanced Stage of Urothelial Differentiation: Association with the Inter–plaque ('Hinge') Area", 1992. Epith. Cell Biol. 1:4–12.*
Yu et al., "Uroplakins Ia and Ib, Two Major Differentiation Products of Bladder Epithelium, Belong to a Family of Four Transmembrane Domain (4TM) Proteins" 1994. J. Cell Biol. 125:171–182.

* cited by examiner

Primary Examiner—Kenneth R. Horlick
Assistant Examiner—Jeffrey Siew
(74) Attorney, Agent, or Firm—Browdy and Neimark

(57) ABSTRACT

The human gene for uroplakin II is identified and sequenced. Using this gene, oligonucleotide primers were constructed which were then used to identify bladder cancer cells in blood and tissue.

8 Claims, No Drawings

HUMAN UROPLAKIN II GENE AND METHODS FOR DETECTING AND CLASSIFYING BLADDER CANCER VIA HUMAN UROPLAKIN GENES

BACKGROUND OF THE INVENTION

Histological differentiation markers are useful in the diagnosis of carcinoma metastases where the location of the primary tumor is uncertain or unknown. Unfortunately, markers specific for a single epithelium or organ are currently available for a only few types of carcinoma, e.g., prostate-specific antigen for prostate carcinomas and thyroglobulin for thyroid carcinomas.

Less specific markers of transitional cell carcinomas have been identified and associated with malignant transformation, tumor progression and the prognosis. Many of these markers are epithelial membrane antigen (EMA) or oncogene/tumor suppressor gene products. For example, Summerhayes et al. (1985. *JNCI* 75:1025–1038) have described a series of monoclonal antibodies (group III), directed against the urothelium which produce luminal-membrane staining of normal superficial (umbrella) cells of the urothelium. Other markers are expressed in superficial bladder tumors but disappear in invasive and metastatic transitional cell carcinomas. All of these markers are antibodies most of which stain non-urinary epithelia and carcinomas too. Certain antigens such as involucrin, E48 antigen and SCC antigen are markers shared by both transitional and stratified squamous epithelia (of skin, esophagus, cervix, etc.) and their carcinomas. However, no differentiation or lineage marker specific for transitional cell carcinomas and their metastases has been identified to date.

Normal urothelium contains tissue-specific differentiation products that have been well characterized morphologically and biochemically. It has been found that large numbers of urothelial plaques are present in the superficial plasma membrane of urothelial superficial or umbrella cells. These plaques are characterized by a highly unusual membrane structure, i.e., the asymmetric unit membrane (AUM), whose luminal leaflet is twice as thick as its cytoplasmic leaflet. The thickening of the luminal leaflet is due to the presence of particles exhibiting a semi-crystalline organization. The molecular constituents principally comprise four transmembrane proteins: uroplakin (UP) Ia (27 kDa); UP Ib (28 kDa); UP II (15 kDa) and UP III (47 kDa). These UPs, particularly UP Ia, Ib, and II, are characterized by their markedly asymmetric mass distribution, with the extracellular domain being considerably larger than the intracellular one. This accounts for the clearly visible ultrastructural thickening of the luminal leaflet of the unit membrane. UP III is believed to play a role in the formation of the urothelial glycocalyx and may interact, via its cytoplasmic portion, with the cytoskeleton.

The identification and characterization of the uroplakins and their role as molecular markers has been described by Yu et al. 1990. *J. Cell Biol.* 111:1207–1216; Wu et al. 1990. *J. Biol. Chem.* 265:19170–19179; Wu et al. 1993. *J. Cell Sci.* 106:31–43; Wu et al. 1994. *J. Biol. Chem.* 269:13716–13724; Yu et al. 1994. *J. Cell Biol.* 125:171–182; and Lin et al. 1994. *J. Biol. Chem.* 269:1775–1784. Further, Ryan et al. (1993. *Mammalian Genome* 4:656–661) describe mapping the chromosomal locations of mouse and bovine UP Ia and UP Ib and suggest likely locations for human genes. The locations of human UP II, UP IIIa and UP IIIb genes are also predicted. Ryan et al. suggest that uroplakin genes could be involved in chronic urinary tract diseases and also suggests diagnostic uses (e.g., interstitial cystitis). Mono-specific antibodies to UP Ia, UP Ib, UP II and UP III were used to show that uroplakin expression is confined to the urinary bladder and to determine the location of UP Ia, UP Ib, UP II and UP III within the asymmetric unit membrane. However, identification, sequencing, or chromosomal location of the human gene for any of the uroplakins has not yet been disclosed.

Yu et al. (1992. *Epith. Cell Biol.* 1:4–b 12) describe the use of specific antibodies to AE31 and AE32 for analysis of the differentiation state of bovine urothelial cells. The diagnostic use of antibodies to uroplakins to positively identify metastatic bladder carcinomas has also been described by Moll, et al. 1993. *Verh. Deutsc. Ges. Path.* 77 and Moll, R. et al. 1995. *Am. J. Pathol.* 147:1383–1397.

The human gene for uroplakin II has now been isolated and sequenced. Using the knowledge of the human uroplakin gene sequence a highly specific uroplakin-based reverse transcriptase (RT)-polymerase chain reaction (PCR) assay has now been developed which is useful in the detection of circulating bladder cancer cells in metastatic bladder cancer patients.

SUMMARY OF THE INVENTION

UP Ia, Ib, II and III are the first molecular markers that have been found to be specific for urothelial differentiation. The human gene sequence of UP II has now been determined. Knowledge of this sequence has been used to develop molecular probes, primer sequences, that are used in a RT-PCR assay to detect the presence of bladder cancer cells in blood and tissues. Accordingly, the assay of the present invention is useful in identifying and diagnosing metastatic bladder cancer cells. Further, the RT-PCR assay can be used to identify mutations in the uroplakin genes.

DETAILED DESCRIPTION OF THE INVENTION

UPs Ia, Ib, II and III are specialized membrane proteins of the urothelial plaque constituting the AUM and represent the first specific molecular markers of urothelial differentiation. UPs are widely conserved with respect to their structural organization and amino acid sequence among all mammals. UP II and III have been found to be immunohistochemically detectable in routinely prepared paraffin sections of human urothelium. Extensive UP III screening of a variety of normal tissues revealed that the urothelium-specificity of this glycoprotein, which until now has been documented only in bovine tissues, is also valid for human tissues. Unlike UP Ia and UP Ib which have 4 putative transmembrane domains (Yu, J. et al. 1994. *J. Cell Biol.* 125:171–182), UP II and UP III have only one transmembrane domain (Lin, J. H. et al. 1994. *J. Biol. Chem.* 269:1775–1784; Wu, X. R. and T. T. Sun. 1993. *J. Cell Sci.* 106:31–43). Recent data indicate that UP II and UP III are preferentially crosslinked to UP Ia and UP Ib, respectively, suggesting the existence of two types of 16 nm AUM particles consisting of UP II/UP Ia and UP III/UP Ib (Wu, X. R. et al. 15 1995. *J. Biol. Chem.* 270:29752–29759).

Mouse and bovine UP II genes have been sequenced. The cDNA-derived amino acid sequences of the mouse and bovine UP II are 83% identical thus indicating a high degree of structural and possibly functional conservation (Wu, X. R. et al. 1995. *J. Biol. Chem.* 270:29752–29759).

The human UP II gene has also now been sequenced. In these experiments, a human genomic library in lambda Fix-II phage (Stratagene, La Jolla, Calif.) was screened with a $^{32}$P-labeled bovine uroplakin II cDNA (Lin, J. H. et al. 1994. *J. Biol. Chem.* 269:1775–1784). Two positive clones were identified. The clone having a longer 5'-flanking sequence was then further characterized. Two Sac I fragments (3.3 kb and 5 kb), that together contained the entire coding region of human uroplakin II gene, were subcloned and sequenced. This sequence is shown as SEQ ID NO: 1. The gene contains 5 exons spanning approximately 2 kb, similar to the mouse and bovine genes. Its deduced amino acid sequence, shown as SEQ ID NO: 2, is 79% identical to those of the mouse and bovine analogues, consisting of a hydrophobic N-terminal signal peptide (approximately 25 amino acid residues) and a prosequence (approximately 59 amino acid residues) harboring 3 potential N-glycosylation sites, and ending with a RGRR cleavage site for furin, which may be involved in UP II processing and maturation, and a mature protein (100 residues) with a C-terminal hydrophobic potential transmembrane domain (approximately 25 residues).

The chromosomal location of human UP II gene has also now been determined. In these experiments, a 21 kb fragment of the human UP II gene containing all five exons was labeled with digoxigenin and used as a probe to hybridize to metaphase chromosomes of human lymphocytes. The initial experiment resulted in specific labeling of the long arm of group C chromosome, which was believed to be chromosome 11 on the basis of DAPI staining. Additional experiments were conducted wherein a biotin-labeled probe from the cyclin D1 locus, which has previously been mapped to 11p13, was co-hybridized with the uroplakin II probe. Specific labeling of the proximal and distal long arm of chromosome 11 was observed. A total of 80 metaphase cells were analyzed, with 59 of these exhibiting specific labeling. Measurements of 10 specifically hybridized chromosomes demonstrated that uroplakin II gene is located at a position which is 82% of the distance from the centromere to the telemere of the long arm of chromosome 11, to the region corresponding to band 11q23.

Oligonucleotides primer pairs corresponding to human uroplakin genes such as UP II can be prepared in accordance with well known techniques. These uroplakin specific oligonucleotide primers are useful in a number of methods.

In one embodiment, oligonucleotide primer pairs corresponding to a selected uroplakin gene can be used to detect the presence of mutations in the selected uroplakin gene. For example, experiments were performed to identify polymorphisms and potential tumor-specific mutations of human UP II gene. In these experiments, SSCP assays were performed on genomic DNAs from 57 cases of human transitional cell carcinomas. PCR was performed using 5 pairs of primers as depicted in Example 1 corresponding to intron sequences that flanked exons 1 to 5. One major mobility-shifted band was identified in exon 2 of the UP II gene in one tumor. This was due to a polymorphism consisting of a G to A substitution at position 114. Additional polymorphisms and potential tumor specific mutations can be identified for human UP II and other uroplakin genes in accordance with this method.

Oligonucleotide primers to human uroplakin genes are also useful in distinguishing different forms of bladder cancer and identifying human bladder cancer cells in blood and tissue. In this embodiment, total RNA is extracted from the blood or tissue cells. The extracted total RNA is then reverse transcribed and amplified by polymerase chain reaction using an oligonucleotide primer complementary to a uroplakin gene so that the presence of the uroplakin RNA in the cell can be detected and human bladder cancer cells identified.

For example, experiments were performed to determine whether different forms of bladder cancer could be distinguished based upon expression of a selected uroplakin genes. In these experiments, two major forms of bladder cancer were considered, transitional cell carcinomas and squamous cell carcinomas. Patients in the study included cases of bilharzial-related bladder cancer (a parasite-related disease), both transitional cell and squamous cell, and conventional transitional cell carcinoma cases. Immunohistochemical staining studies were first performed using a rabbit antiserum to a synthetic peptide corresponding to amino acid residues 7-19 located at the N-terminus of mature UP II. This antibody has previously been shown to be monospecific for UP II by immunoblotting (Lin, J. H. et al. 1994. *J. Biol. Chem.* 269:1775–1784). Results of these experiments showed that 40% of the transitional cell carcinoma specimens were uroplakin II-30 positive.

Based upon this information indicating that UP II gene is present in the majority of transitional cell carcinomas, an RT-PCR assay for detection of blood-borne tumor cell dissemination by UP II detection in patients with transitional cell carcinoma was developed. Various specific oligonucleotide primers for human uroplakin II as described in Example 5 were designed on the basis of the sequence of the human UP II gene. Two primer pairs were identified which were particularly effective in amplifying UP II mRNA from the specimens. These primers are located in exons 2 (UP II outer sense and nested sense; SEQ ID NOs: 14 and 15, respectively) and exon 4 (UP II outer antisense and nested antisense; SEQ ID NOs: 21 and 22, respectively). The outer primers produce a PCR fragment of 330 bp while the nested primers produce a fragment of 270 bp.

The PCR products were then cloned into the PCRII plasmid vector using the TA cloning system. These plasmids were then transformed into competent *E. coli* cells using standard methods. Plasmid DNA was then isolated and screened by restriction analysis using EcoRI. The TA clones were sequenced by the dideoxy method using SP6 and T7 primers. These sequences were compared to the original human UP II DNA sequence (SEQ ID NO: 1).

Total RNAs were extracted from peripheral blood of patients with transitional cell carcinoma. The RNAs were then reverse-transcribed and subjected to PCR amplification using the identified oligonucleotide primers. As controls, RNAs were also extracted from normal blood, normal tissue, and bladder cancer specimens.

Results showed that UP II mRNAs were only amplified in normal urothelium and transitional cell carcinoma tissue. The response was specific in that there was no response in negative control tissues (human prostate, skin, ovary, uterus, liver, and blood). All 10 (2 superficial and 8 invasive) transitional cell carcinoma tissue specimens were positive for UP II. In the blood samples from patients with transitional cell carcinoma, the RT-PCR assay was used to identify metastasized cells. Of the 50 non-metastatic patients, none of the blood samples were positive for UP II. In contrast, 2 of 10 of the metastatic blood samples were positive for UP II. Southern blotting and DNA sequencing established that the PCR products amplified from these two patients were UP II sequence. Accordingly, the UP II primers of the present invention are useful for the identification of blood-borne bladder cancer cells and in the diagnosis of metastatic disease at an early stage.

As will be obvious to those of skill in the art upon this disclosure, similar RT-PCR methods for other uroplakin genes can be developed in accordance with the methods described herein based upon the detection of other uroplakin genes. Based upon the teachings provided herein, one of skill could routinely screen the human genomic library for other uroplakin genes (i. e., III, Ia, and Ib) to develop specific oligonucleotide primers for screening for different types of bladder cancer.

The following nonlimiting examples are presented to illustrate the claimed invention.

EXAMPLES

Example 1
Genomic Cloning and Single Strand Conformation Polymorphism

A human genomic library in lamda Fix-II phage (Stratagene, La Jolla, Calif.) was screened with a $^{32}$P-labeled bovine uroplakin-II cDNA described by Lin, J. H. et al. 1994. *J. Biol. Chem.* 269:1775–84. PCR-SSCP assays were performed on a subset of 57 bladder tumors using a modification of the method described by Orita, M. et al. 1989. Genomics 5:874–879 and Cordon-Cardom C. et al. 1994. Int. J. Cancer 56:347–353. The sequences of the five sets of PCR primers used to amplify exons 1–5 of the human uroplakin II gene are as follows:

```
Exon 1:  5'-CTGCCAGCACCTATTCCACCTC-3' (SEQ ID NO:3)

5'-CCATCGGAGCTCCCTCTGC-3'    (SEQ ID NO:4)

Exon 2:  5'-CCATCGGAGCTCCCTCTGC-3'    (SEQ ID NO:5)

5'-GGGACTAGAGGGATGCCTTG-3'   (SEQ ID NO:6)

Exon 3:  5'-GAAACTTGACCCAGTCTTCC-3'   (SEQ ID NO:7)

5'-CTTCCCTAGGTGCCTCAGG-3'    (SEQ ID NO:8)

Exon 4:  5'-CTCTTCCTGTAAGTCCCAATAC-3' (SEQ ID NO:9)

5'-GAATGGTCAGGGAAGCGTTTG-3'  (SEQ ID NO:10)

Exon 5:  5'-CCACAGTGGTCTCCCCTCTC-3'   (SEQ ID NO:11)

5'-CTGGAGAAGCTGCTGCTCCG-3'   (SEQ ID NO:12)
```

Each PCR reaction mixture contained 100 ng of tumor genomic DNA in 10 μl of 10 mM Tris-HDl (pH 8.3), 50 mM KCl, 2.5 mM MgCl$_2$, 250 μM each of cold deoxynucleotide-5'-triphosphate, 1.5 μM of each PCR primer, 0.5 unit of Tag DNA-polymerase, and 01 μl of $^{33}$P-dCTP (NEN, Cambridge, Mass.). PCR reactions were performed using a Thermal Cycler (Perkin-Elmer Cetus, Foster City, Calif.) by denaturation at 94° C. for 3 minutes, followed by 40 cycles of amplification (45 seconds at 94° C., 45 seconds at 65° C. and 45 seconds at 72° C.) and were then kept at 72° C. for 3 minutes. The PCR products were denatured and loaded onto a denaturing 8% MDE polyacrylamide gel (J. T. Baker, Phillipsburg, N.J.) and electrophoresed at room temperature for 14 to 18 hours. After electrophoresis, the gels were dried and exposed to X-ray film at 70° C. overnight. Mobility-shifted DNA bands wee reamplified and directly sequenced by the dideoxy method described by Sanger, F. et al. 1977. *Proc. Natl Acad. Sci. USA* 74:5463–5467.

Example 2
Fluorescence In Situ Hybridization

A human uroplakin II genomic fragment was labeled with digoxigenin-dUTP by nick translation (Genome systems, St. Louis, Mo.). The labeled probes were combined with sheared human DNA and hybridized to normal metaphase chromosomes derived from PHA-stimulated peripheral blood lymphocytes from a male donor in a solution containing 50% formamide, 10% dextran sulfate and 2×SSC. Specific signals for one-color experiments were detected by incubating the hybridized specimens with fluoresceinated anti-digoxigenin antibodies followed by counter-staining with DAPI. Two-color experiments were conducted using the same protocol, except for the inclusion of Texas Red-labeled avidin as described by Stokke, T. et al. 1995 *Genomics* 26:134–7.

A cohort of 121 patients with primary bladder tumors wee evaluated. Seventy-eight cases were bilharzial-related bladder cancer; these samples were obtained from the Pathology Department at the National Cancer Institute in Cairo, Egypt. Schistosomiases infection was confirmed in all these 78 cases by the presence of ova on histological sections. Forty-two of these cases were transitional cell carcinomas, while the remaining 36 were squamous cell carcinomas. An additional forty-three cases of conventional transitional cell carcinoma were obtained from the Pathology Department at the Memorial-Sloan Kettering cancer center in New York. Hematoxylin-eosin stained sections of all cases were examined to evaluate the pathological type, tumor grade and stage. Tumors were staged as Pis (carcinoma in situ; 1 case), P1 (17 cases), P2 (4 cases), P3 (92 cases) and P4 (7 cases). Twenty-five tumors were classified as low grade (grade 1), 71 as intermediate grade (grade 2) and 25 as high grade (grade 3).

Example 3
Immunohistochemical Techniques

Three rabbit antisera against uroplakin proteins or peptides were used in this study. First, a rabbit antiserum was generated against total uroplakins of highly purified bovine AUM; this antiserum reacts strongly with the 47-kD uroplakin III, moderately with the 27-kD uroplakin Ib, and weakly with the 15-kD uroplakin II as disclosed by Wu, X. R. and Sun, T. T. 1993 *J. Cell Science* 106:31–43 and Wu, X. R. et al. 1994 *J. Biol. Chem.* 269:13716–24. Second, an anti-47-kDa antibody was affinity-purified from the above anti-total uroplakins against the electrophoretically purified 47-kD uroplakin band as disclosed by Wu, X. R. and Sun, T. T. 1993 *J. Cell Science* 106:31–43 and Wu, X. R. et al. 1990. *J. Biol. Chem.* 265:19170–9. Third, a rabbit antiserum was raised against a synthetic peptide corresponding to amino acid residues 7–19 (DSGSGFTVTRLLA (SEQ ID NO: 13)) of the mature bovine uroplakin as described by Lin, J. H. et al. 1994. *J. Biol. Chem.* 269:1775–84. The latter two antibodies were shown to be monospecific for the 47-kD UP III and the 15-kD UP II, respectively, by immunoblotting.

Avidin-biotin immunohistochemical staining was performed as described by Osman, I. et al. 1997 *Clin. Can. Res.* 3:531–35 536. In this method, deparaffinized tissue sections were treated with 1% hydrogen peroxide in phosphate-buffered saline (PBS) to block the endogenous peroxidase activity, incubated with normal goat serum (diluted 1:10 in 2% bovine serum albumin or BSA), followed by overnight incubation at 4° C. with various antisera to uroplakins (diluted 1:10,000 in 2% BSA/PBS). Biotinylated goat anti-rabbit IgG was applied for 1 hour at 25° C., 1:800 (Vector Laboratories, Burlingame, Calif.), followed by avidin-biotin peroxidase complexes for 30 minutes, 1:25 dilution (Vector Laboratories). Diaminobenzidine and hematoxylin were used as the final chromogen and nuclear counter-stain, respectively. The immunoreactivities were classified as positive if more than 20% tumor cells showed positive membrane and cytoplasmic Staining.

The associations between the uroplakin expression patterns and clinicopathological parameters, including tumor stage, grade, and tumor type, were assessed by Fisher's Exact test as described by Metha, C. R. and Patel, N. R. 1983. *J. Am. Stat. Assoc.* 78:427–434; the two tailed p-values were employed to assess the significance level. For variables with more than two categories, the dose-response relationship was assessed by the trend-test using the Mantel-Haenszel method as described by Landis, R. J. et al. 1978 *Int. Stat. Rev.* 46:237–b 254. The FREQ procedure in SAS was used for analyzing the data as described in accordance with the SAS/STAT Use Guide.

Example 4

Blood Sample Processing and RNA Extraction

All blood specimens used in the study were from patients seen at the New York University Medical Center. Specimen procurement was conducted according to the approval of the institutional review board. Two heparinized (blue top) tubes per patient were obtained via venipuncture technique. Samples were promptly brought to the laboratory on ice for immediate proceeding. A total of 50 nonmetastatic and 10 metastatic blood from patients with bladder cancer were obtained. The 6 blood specimens used as negative controls wee from healthy volunteers. In addition, 10 bladder tumor tissues were obtained after specimens were removed from either radical cystoprostatectomy or transurethrally.

RNA extraction was performed using the RNAgents Total RNA Isolation System by Promega. A total of 5 ml whole anticoagulated venous blood was mixed with 1.5×volume of ice cold diethylpyrocarbonate-treated water. After 5 minutes of incubation, the samples were centrifuged for 20 minutes at 10,000 rpm at 4° C. in a 50 ml polystyrene tube. After decanting the supernatant, the platelet was washed with 1.5×volume ice cold 1×phosphate buffered solution and centrifuged for 15 minutes at 10,000 rpm at 4° C. The supernatant was carefully decanted and the pellet was resuspended with 5 ml of denaturing buffer, 0.5 ml of 2 M NaAcetate (pH 4.0), and 5 ml of Phenol:Chloroform:I-soamyl alcohol. This tube was incubated on ice for 15 minutes and then centrifuged for 20 minutes at 10,000 rpm at 4° C. The supernatant was carefully isolated and was mixed with an equal volume of isopropanol. This mixture was incubated at −20° C. overnight.

The solution was centrifuged for 15 minute at 10,000 rpm at 4° C. The pellet was resuspended in 1 ml of denaturing buffer and 1 ml of isopropanol. The mixture was incubated at −20° C. for 2 hours and transferred to two eppendorf tubes. This solution was centrifuged for 15 minutes at 10,000 rpm at 4° C. The collected pellet was washed with 0.5 ml of 75% ethanol and then centrifuged for 15 minutes at 10,000 rpm at 4° C. The supernatant was decanted and the pellet was dried at room temperature for 10 minutes. The RNA pellet was dissolved in 30 $\mu$l of RNAse-free water. TNA concentrations and purity were determined by ultraviolet spectrophotometer. Approximately 15–25 $\mu$g of RNAs was extracted from 5 ml of human whole blood. Bladder tissue specimens were homogenized initially and RNA was extracted in a similar method.

Example 5

Polymerase Chain Reaction Assay

Specific oligonucleotide primers for human uroplakin II were designed on the basis of SEQ ID NO: 1. Ten different primer pairs were selected to locate in different exons as described in Example 1. Two pair of primers were identified that were most effective in amplifying UP II mRNA from these specimens. The primers were located in exons 2 (UP II outer sense and nested sense), exons 4 (UP II outer antisense and nested antisense). The outer primers produce a PCR fragment of 320 bp and the nested primers a fragment of 270 bp.

Upon the recommendation of the manufacturer Promega and using the Reverse Transcription Kit, 1 $\mu$g of the total RNA was reversely transcribed into complementary DNA. The total volume of the reaction was 20 $\mu$l, consisting of 2 $\mu$l of 10×RT buffer, 4 $\mu$l of 25 mM MgCl2, 2 $\mu$l of 10 mM DNTP mix, 0.5 $\mu$l of rRNAsin ribonuclease inhibitor (1 unit/$\mu$l), 0.6 $\mu$l of AMV transcriptase (15 units/$\mu$l), 0.5 $\mu$l of oligo dTprimers, and RNAse free water. The reaction was incubated at 42° C. for 25 minutes, heated at 99° C. for 5 minutes and then placed on ice immediately.

The polymerase chain reaction was performed in a total volume of 50 $\mu$l containing 1.5 $\mu$l of the complementary DNA, 1.5 units of Tag polymerase, Promega buffer solution, 100 $\mu$M of each deoxynucleotide triphosphates and 10 ng of each primer. This mix with the outer sense and outer antisense was transferred to a Perkin-Elmer model PCR machine. The polymerase chain reaction profile was (a) 1 cycle of 94° C. for 5 minutes, then 60° C. for 1 minute, then 72° C. for 2 minutes; (b) 5 cycles of 94° C. for 2 minutes, then 60° C. for 1 minute, then 72° C. for 2 minutes; (c) 1 cycle of 94° C. for 2 minutes, then 60° C. for 1 minute, then 72° C. for 8 minutes. For reamplification, 2.5 $\mu$l of the first PCR product was further amplified with the nested primers in a 50 $\mu$l reaction volume under the same condition for 35 cycles. Fifteen microliters of the product were electrophoresed on a 1.5% agarose gel and visualized by ethidium bromide staining.

Polymerase chain reaction products were cloned into the PCRII plasmid vector using the TA cloning system. These plasmids were transformed into competent *Escherichia coli* cells using standard methods; plasmid DNA was isolated and screened by restriction analysis using EcoRI. The TA clones were then sequenced by the dideoxy method using SP6 and T7 primers. These sequences were then compared to the original Human Uroplakin II DNA sequence.

Example 6

Southern Transfer Analysis

A 1.2% agarose gel containing the samples was soaked with 0.25 M HCl solution for 30 minutes followed by 1.5 M NaCl mixed with 0.5 M NaOH for 20 minutes, twice. The gels were then pressure blotted on nylon membrane overnight. The membranes were then soaked and rinsed with 2×SSC twice, and then crosslinked with the ultraviolet Stratalinker for 1 minute. The blots were prehybridized at 60° C. for three hours and eventually hybridized with $^{32}$P-labelled human uroplakin complementary DNA probes overnight. The membranes were then washed twice with the low stringent buffer solution of 0.15 M NaP/0.1% sodium dodecyl sulfate at 60° C. for 20 minutes. The membranes were then air dried and autoradiographed for 2 hours at 70° C.

The following is a list of primers used for PCR. amplification. Primers HUPS1 and HUPAS4 were found to be the most effective in amplifying UP II mRNA from blood of metastatic bladder cancer patients.

Human Uroplakin II Sense Primer

HUPS1  5'-AACATCTCAAGCCTCTCTGGTCTG-3'
(SEQ ID NO: 14) (outer sense primer)

HUPS2  5'-TGTCACCTCACAGGAGGCAATGCC-3'
(SEQ ID NO: 15) (nested sense primer)

HUPS3  5'-ACTGATGGTCCGGAGAGCCAATGA-3'
(SEQ ID NO: 16)

HUPS4 5'-GTCCCCGGCGCTAACGGAGAGCCTG-3' (SEQ ID NO: 17)

Human Uroplakin II Antisense Primers

HUPAS1 5'-AGCCCAGTGCCAGGGCAATGATGAA-3' (SEQ ID NO: 18)

HUPAS2 5'-CCACCAGCAGGAACATGGCGACAGAG-3' (SEQ ID NO: 19)

HUPAS3 5'-CAGCACCGTGATGACCACCATGCCC-3' (SEQ ID NO: 20)

HUPAS4 5'-TGTGGACATTGGGATCTCTCTGCTG-3' (SEQ ID NO: 21) (outer antisense primer)

HUPAS5 5'-GCTGTCCCCTTCTTCACTAGGTAGG-3' (SEQ ID NO: 22) (nested antisense primer)

Human Uroplakin II DNA Probe

5'-TGCCGTGGGCGCAGGGAACTGGTGAG TGTGGTGGACAGTGGTGCTGGCTTCACAGTC ACT-3' (SEQ ID NO: 23)

---

What is claimed is:

1. An isolated, purified DNA encoding human uroplakin II comprising SEQ ID NO: 1.

2. An oligonucleotide primer complementary to a strand of the human uroplakin II gene and having a nucleotide sequence selected from the group consisting of SEQ ID NOs: 14, 15, 21, and 22.

3. A method for identifying human bladder cancer cells, comprising:
   a) extracting total RNA from human blood or tissue cells;
   b) reverse transcribing the extracted total RNA;
   c) amplifying the reverse transcribed total RNA by polymerase chain reaction using one or more pairs of oligonucleotide primers complementary to the human uroplakin II DNA of claim 1; and
   d) detecting the presence of human uroplakin II RNA in the cell so that human bladder cancer cells are identified.

4. A method for detecting the presence of mutations in the DNA of claim 1, comprising detecting in a DNA sample, via polymerase chain reaction-single strand conformation polymorphism methods that employ oligonucleotide primers complementary to the DNA of claim 1, mobility-shifted bands, wherein the mobility-shifted bands are indicative of a mutation in the DNA of claim 1.

5. The method according to claim 3, wherein said RNA extracting step extracts RNA from human blood cells.

6. The method according to claim 3, wherein said RNA extracting step extracts RNA from human tissue cells.

7. The method according to claim 3, wherein, in said amplifying step, the one or more pairs of oligonucleotide primers is selected from the group consisting of SEQ ID NOs: 14, 16, 21, and 22.

8. An isolated DNA molecule encoding the human uroplakin II amino acid sequence of SEQ ID NO:2.

* * * * *

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
      (A) LENGTH: 2439
      (B) TYPE: NUCLEIC ACID
      (C) STRANDEDNESS: SINGLE
      (D) TOPOLOGY: LINEAR (iv) ANTI-SENSE: NO (xi) SEQUENCE DESCRIPTION: SEQ ID NO: 1:

```
CCCAAGGGGC AGGTTGGACT GGATTCCCCT CCAGCCCCTC CCACCCNCAG           50

GACAAAATCA GCCACCCCAG GGGCAGGGCC TCACTTGCCT CAGGAACCCC          100

AGCCTGCCAG CACCTATTCC ACCTCCCAGC CCAGCATGGC ACCCCTGCTG          150

CCCATCCGGA CCTTGCCCTT GATCCTGATT CTGCTGGCTC TGCTGTCCCC          200

AGGGGCTGCA GGTCTCTTCC ATCTCTGGCA GGGGTGGGAA GGGGGCTGGG          250

GGCCTGGACA GGGAGCACTG TACCTTCCAG GGCTCTCAAA NANAGGTCTG          300

GACAGTTGGG AGTCAGGGCT GGTGATGGCA GTGACTGGGT ATCAAACACT          350

GGGCTCAGGG TACACTCCTG ATCCTCCTCC AAACCTAGGA GGCAAANAGG          400

TGTGGGCAAG GATCCGATGC TGCGGGGAGG GGTGAGGTTG GGCGCTGCCC          450

GACTCCTGGC ATCCAGGTTC TGGCTCTGGG GACCGCTTGG TGGAGGGTGC          500

AGCTTCTGCA GCCCAAGCCT GCCACCTGGT GGTCATACTG GCACAGGCCT          550

GGCTGTTCTG CCCAGGGTTC ACANAGTGGA AAGGGAGATG GCTCCAATGG          600

GACCGGGCCA AATCTGTTGG CCANGAAGGG TCANTCCCAT CGGAGCTCCC          650

TCCTGCCTCC CATCAGACTT CAACATCTCA AGCCTCTCTG GTCTGCTGTC          700

CCCGGCGCTA ACGGAGAGCC TGCTGGTTGC CTTGCCCCCC TGTCACCTCA          750

CAGGAGGCAA TGCCACACTG ATGGTCCGGA GAGCCAATGA CAGCAAAGGT          800

CTGCTACCTT CTCCCAAGGC ATCCCTCTAG TCCCCAAAGA CCCCTTCCTG          850

CGACACCCTC TGCACCCTTT TCCCCATTCA TGCCTTCCTG TCCACCCGTC          900

TCCTGGGGTA CCCACACTCT AAAAGCTGCC CCTTCTCCTT GGGGCCTCCA          950

GAAACTTGAC CCAGTCTTCC CCTCCCGCCA CTTCTGCCCA GTGGTGACGT         1000

CCAGCTTTGT GGTGCCTCCG TGCCGTGGGC GCAGGGAACT GGTGAGTGTG         1050

GTGGACAGTG GTGCTGGCTT CACAGTCACT CGGCTCAGTG CATACCAGGT         1100

GACAAACCTC GTGCCAGGAA CCAAATTCTA GTAGGTACTG GTCCAGCCT          1150
```

-continued

```
GAGGCACCTA GGGAAGGGGG TGCAGGAAGA GAGAGAAGCT AGTGTGGGGG         1200

AGATCTGGTG GGCATGAGGA GAGGGTGAGG GCACAGCAAA AGGGGGTGAA         1250

AGCTGGGACT CTTGGAGGAN TGCACATATG GGAGACACAN CTGTTAAGGT         1300

NTGTGGCCCA TGCTGGAGCC CCTCTTCCTG TAAGTCCCAA TACTCACTGA         1350

GGTTCTCTAC TTTCTCCCAA ACCACAAAAG CATTTCCTAC CTAGTGAAGA         1400

AGGGGACAGC CACTGAGTCC AGCAGAGAGA TCCCAATGTC CACACTCCCT         1450

CGTAAGTAAC ACTCCCGCCT CCCTTTCCCA TCTCAGCGGC CACAAACGCT         1500

TCCCTGACCA TTCCTGCCTC ATCCCCAGTC TGGGTTGCCT GTGCCTCCCC         1550

GTGCGCCCTC GGGGCCCCTG CTTACCTCTA TCCTAGCACG GAACCTTCGG         1600

CATGGCTACT GCACACTCAG CTAAAGGTTC CTCGTGGGCA GGGACTGTGT         1650

CCTCTTAACT TTTCCTCAGC GGCTGACATA NGAGATGCTT CATAAATGTC         1700

TATGTGATGG GTGTTTGGAT CCATCAGCTG GTTGGTTGGT TGGTTGGTTG         1750

GNAGGCTGGN TGGCTGGCTG GNTGGATGGT TGGTTGGGCA GTCTGTTGGC         1800

TGGATGAGTG TGAGGCCGTG AGCCTCAGGC AGGCTGGGGG TCTCTCCCGC         1850

CCACAGTGGT CTCCCCTCTC TTTTGACAGG AAGGAACATG CAATCCATTG         1900

GGCTGGGTAT GGCCCGCACA GGGGGCATGG TGGTCATCAC GGTGCTGCTC         1950

TCTGTCGCCA TGTTCCTGCT GGTGCTGGGC TTCATCATTG CCCTGGCACT         2000

GGGCTCCCGC AAGTAAGGAG GTCTGCCCGG AGCAGCAGCT TCTCCAGNAA         2050

GCCCAGGGCA CCATCCAGCT CCCCAGCCCA CCTGCTCCCA GGCCCCAGGC         2100

CTGTGGCTCC CTTGGTGCCC TCGCCTCCTC CTCCTGCCCT CCTCTCCCCT         2150

AAAGCCCTCT CCTCCCTCTG TCCCTCTCCT TGCCCCCAGT GCCTCACCTT         2200

CCAACACTCC ATTATTCCTC TCACCCCACT CCTGTCAGAG TTGATTTCCT         2250

CCCATTTTAC CACTTTAAAC ACCCCCATAA CAATTCCCCC ATCCTTCAGT         2300

GAACTAAGTC CCTATAATAA AGGCTGAGGC TGCATCTGCC ACATGTGTTT         2350

CCCTTTAGTG GGCTCTACCT TGGCTCAAAC CTGTGGAATC TATGTCCAAG         2400

CTGCAGGTGC TCCTGGTCCC CTCCCTGCCC CACAGCCCA                     2439
```

(2) INFORMATION FOR SEQ ID NO: 2:

(i) SEQUENCE CHARACTERISTICS:
        (A) LENGTH: 184
        (B) TYPE: AMINO ACID
        (D) TOPOLOGY: LINEAR (xi) SEQUENCE DESCRIPTION: SEQ ID NO: 2:

```
MET ALA PRO LEU LEU PRO ILE ARG THR LEU PRO LEU ILE LEU ILE
1               5                   10                  15

LEU LEU ALA LEU LEU SER PRO GLY ALA ALA ASP PHE ASN ILE SER
                20                  25                  30

SER LEU SER GLY LEU LEU SER PRO ALA LEU THR GLU SER LEU LEU
                35                  40                  45

VAL ALA LEU PRO PRO CYS HIS LEU THR GLY GLY ASN ALA THR LEU
                50                  55                  60

MET VAL ARG ARG ALA ASN ASP SER LYS VAL VAL THR SER SER PHE
                65                  70                  75

VAL VAL PRO PRO CYS ARG GLY ARG ARG GLU LEU VAL SER VAL VAL
```

```
                        80                  85                  90
ASP SER GLY ALA GLY PHE THR VAL THR ARG LEU SER ALA TYR GLN
                        95                 100                 105
VAL THR ASN LEU VAL PRO GLY THR LYS PHE TYR ILE SER TYR LEU
                       110                 115                 120
VAL LYS LYS GLY THR ALA THR GLU SER SER ARG GLU ILE PRO MET
                       125                 130                 135
SER THR LEU PRO ARG ARG ASN MET GLU SER ILE GLY LEU GLY MET
                       140                 145                 150
ALA ARG THR GLY GLY MET VAL VAL ILE THR VAL LEU LEU SER VAL
                       155                 160                 165
ALA MET PHE LEU LEU VAL LEU GLY PHE ILE ILE ALA LEU ALA LEU
                       170                 175                 180
GLY SER ARG LYS (2) INFORMATION FOR SEQ ID NO: 3:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 3:

CTGCCAGCAC CTATTCCACC TC                                              22

(2) INFORMATION FOR SEQ ID NO: 4:

(i) SEQUENCE CHARACTERISTICS:
        (A) LENGTH: 19
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 4:

CCATCGGAGC TCCCTCTGC                                                  19

(2) INFORMATION FOR SEQ ID NO: 5:

(i) SEQUENCE CHARACTERISTICS:
        (A) LENGTH: 19
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 5:

CCATCGGAGC TCCCTCTGC                                                  19

(2) INFORMATION FOR SEQ ID NO: 6:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 6:
```

GGGACTAGAG GGATGCCTTG                                                      20

(2) INFORMATION FOR SEQ ID NO: 7:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 7:

GAAACTTGAC CCAGTCTTCC                                                      20

(2) INFORMATION FOR SEQ ID NO: 8:

(i) SEQUENCE CHARACTERISTICS:
        (A) LENGTH: 19
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 8:

CTTCCCTAGG TGCCTCAGG                                                       19

(2) INFORMATION FOR SEQ ID NO: 9:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 9:

CTCTTCCTGT AAGTCCCAAT AC                                                   22

(2) INFORMATION FOR SEQ ID NO: 10:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 10:

GAATGGTCAG GGAAGCGTTT G                                                    21

(2) INFORMATION FOR SEQ ID NO: 11:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 11:

CCACAGTGGT CTCCCCTCTC                                                      20

(2) INFORMATION FOR SEQ ID NO: 12:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 12:

CTGGAGAAGC TGCTGCTCCG                                  20

(2) INFORMATION FOR SEQ ID NO: 13:

(i) SEQUENCE CHARACTERISTICS:
        (A) LENGTH: 13
        (B) TYPE: AMINO ACID
        (D) TOPOLOGY: LINEAR (xi) SEQUENCE DESCRIPTION: SEQ ID NO: 13:

ASP SER GLY SER GLY PHE THR VAL THR ARG LEU LEU ALA
                5                   10

(2) INFORMATION FOR SEQ ID NO: 14:

(i) SEQUENCE CHARACTERISTICS:
        (A) LENGTH: 24
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 14:

AACATCTCAA GCCTCTCTGG TCTG                            24

(2) INFORMATION FOR SEQ ID NO: 15:

(i) SEQUENCE CHARACTERISTICS:
        (A) LENGTH: 24
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 15:

TGTCACCTCA CAGGAGGCAA TGCC                            24

(2) INFORMATION FOR SEQ ID NO: 16:

(i) SEQUENCE CHARACTERISTICS:
        (A) LENGTH: 24
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 16:

ACTGATGGTC CGGAGAGCCA ATGA                            24

(2) INFORMATION FOR SEQ ID NO: 17:

(i) SEQUENCE CHARACTERISTICS:
        (A) LENGTH: 25
        (B) TYPE: NUCLEIC ACID
        (C) STRANDEDNESS: SINGLE (D) TOPOLOGY:  LINEAR (iv) ANTI-SENSE:  NO (xi) SEQUENCE DESCRIPTION:  SEQ ID NO: 17:

GTCCCCGGCG CTAACGGAGA GCCTG                                              25

(2) INFORMATION FOR SEQ ID NO: 18:

(i) SEQUENCE CHARACTERISTICS:
        (A) LENGTH:  25
        (B) TYPE:  NUCLEIC ACID
        (C) STRANDEDNESS:  SINGLE
        (D) TOPOLOGY:  LINEAR (iv) ANTI-SENSE:  YES (xi) SEQUENCE DESCRIPTION:  SEQ ID NO: 18:

AGCCCAGTGC CAGGGCAATG ATGAA                                              25

(2) INFORMATION FOR SEQ ID NO: 19:

(i) SEQUENCE CHARACTERISTICS:
        (A) LENGTH:  26
        (B) TYPE:  NUCLEIC ACID
        (C) STRANDEDNESS:  SINGLE
        (D) TOPOLOGY:  LINEAR (iv) ANTI-SENSE:  YES (xi) SEQUENCE DESCRIPTION:  SEQ ID NO: 19:

GCACCAGCAG GAACATGGCG ACAGAG                                             26

(2) INFORMATION FOR SEQ ID NO: 20:

(i) SEQUENCE CHARACTERISTICS:
        (A) LENGTH:  25
        (B) TYPE:  NUCLEIC ACID
        (C) STRANDEDNESS:  SINGLE
        (D) TOPOLOGY:  LINEAR (iv) ANTI-SENSE:  YES (xi) SEQUENCE DESCRIPTION:  SEQ ID NO: 20:

CAGCACCGTG ATGACCACCA TGCCC                                              25

(2) INFORMATION FOR SEQ ID NO: 21:

(i) SEQUENCE CHARACTERISTICS:
        (A) LENGTH:  25
        (B) TYPE:  NUCLEIC ACID
        (C) STRANDEDNESS:  SINGLE
        (D) TOPOLOGY:  LINEAR (iv) ANTI-SENSE:  YES (xi) SEQUENCE DESCRIPTION:  SEQ ID NO: 21:

TGTGGACATT GGGATCTCTC TGCTG                                              25

(2) INFORMATION FOR SEQ ID NO: 22:

(i) SEQUENCE CHARACTERISTICS:
        (A) LENGTH:  25
        (B) TYPE:  NUCLEIC ACID
        (C) STRANDEDNESS:  SINGLE
        (D) TOPOLOGY:  LINEAR (iv) ANTI-SENSE:  YES

-continued

```
    (xi) SEQUENCE DESCRIPTION: SEQ ID NO: 22:

GCTGTCCCCT TCTTCACTAG GTAGG                                         25

(2) INFORMATION FOR SEQ ID NO: 23:

(i) SEQUENCE CHARACTERISTICS:
        (A) LENGTH:  60
        (B) TYPE:  NUCLEIC ACID
        (C) STRANDEDNESS:  SINGLE
        (D) TOPOLOGY:  LINEAR (iv) ANTI-SENSE:  NO (xi) SEQUENCE DESCRIPTION: SEQ ID NO: 23:

TGCCGTGGGC GCAGGGAACT GGTGAGTGTG GTGGACAGTG GTGCTGGCTT              50

CACAGTCACT                                                          60
```